(12) United States Patent
Duffy et al.

(10) Patent No.: US 7,718,778 B2
(45) Date of Patent: May 18, 2010

(54) ANTIBODY REACTIVE WITH HUMAN TOLL LIKE RECEPTOR 3

(75) Inventors: Karen E. Duffy, Trappe, PA (US); Chong C. Huang, Paoli, PA (US); Roberta Lamb, Wynnewood, PA (US); Mouhamadou L. Mbow, King of Prussia, PA (US); Robert T. Sarisky, Lansdale, PA (US); Lani San Mateo, Devon, PA (US)

(73) Assignee: Centocor, Inc., Malvern, PA (US)

( * ) Notice: Subject to any disclaimer, the term of this patent is extended or adjusted under 35 U.S.C. 154(b) by 4 days.

(21) Appl. No.: 11/553,633

(22) Filed: Oct. 27, 2006

(65) Prior Publication Data

US 2007/0098716 A1 May 3, 2007

Related U.S. Application Data

(60) Provisional application No. 60/730,793, filed on Oct. 27, 2005.

(51) Int. Cl.
*C07K 16/00* (2006.01)
*C07K 16/28* (2006.01)
*C12N 5/20* (2006.01)

(52) U.S. Cl. .............................. 530/388.22; 530/387.1; 530/388.1; 435/326

(58) Field of Classification Search ........................ None
See application file for complete search history.

(56) References Cited

U.S. PATENT DOCUMENTS

| 5,225,539 | A | 7/1993 | Winter | |
|---|---|---|---|---|
| 2003/0032090 | A1* | 2/2003 | Hardiman et al. | 435/69.1 |
| 2004/0091491 | A1 | 5/2004 | Kedl et al. | |
| 2005/0106142 | A1 | 5/2005 | Marshak-Rothstein et al. | |
| 2005/0112659 | A1 | 5/2005 | Hardiman et al. | |
| 2005/0158799 | A1 | 7/2005 | Fitzgerald et al. | |
| 2006/0115475 | A1* | 6/2006 | Carton et al. | 424/143.1 |

FOREIGN PATENT DOCUMENTS

| EP | 1 495 756 A1 | 1/2005 |
|---|---|---|
| EP | 1 887 014 A1 | 2/2008 |
| WO | WO 98/50547 A2 | 11/1998 |
| WO | WO 00/53165 A2 | 9/2000 |
| WO | WO 00/53224 A2 | 9/2000 |
| WO | WO 01/47543 A2 | 7/2001 |
| WO | WO 03/031573 A2 | 4/2003 |

OTHER PUBLICATIONS

Rudikoff et al. PNAS 1982 vol. 79, pp. 1979-1983.*
Rader et al. PNAS. 1998. 95:8910-8915.*
Akira, et al., "Recognition of pathogen-associated molecular patterns by TLR family," Immunology Letters, 85: 85-95 (2003).
Alexopoulou, et al., "Recognition of double-stranded RNA and activation of NF-κB by Toll-like receptor 3," Nature, 413: 732-738 (2001).
Bausinger, et al., "Endotoxin-free heat-shock protein 70 fails to induce APC activation," European Journal of Immunology, 32: 3708-3713 (2002).
Barton, et al., "Toll-Like Receptor Signaling Pathways," Science, 300, 1524-1525 (2003).
Banchereau, et al., "Dendritic cells and the control of immunity," Nature, 392: 245-252 (1998).
Banchereau, et al., "Immunobiology of Dendritic Cells," Annual Review of Immunology, 18: 767-811 (2000).
Bechar, et al., "Toll-like receptor stimulation induces airway hyper-responsiveness to bradykinin, an effect mediated by JNK and NF-κB signaling pathways," European Journal of Immunolgy, 34: 1196-1207 (2004).
Zhou, et al., "CD14+blood monocres can differentiate into functionally mature CD83+dendritic cells,"Proceedings of the National Academy of Science USA, 93: 2588-2592 (1996).
Tabeta, et al., "Toll-like receptors 9 and 3 as essential components of innate immune defense against mouse cytomegalovirus infection," Proceedings of the National Academy of Science USA, 101(10): 3516-3521 (2004).
Gerald B. Pier, "Role of the cystic fibrosis transmembrane conductance regulator in innate immunity to *Pseudomonas aeruginosa* infections," Proceedings of the National Academy of Science USA, 97(16): 8822-8828(2000).
Beil, et al., "The molecular structure of the Toll-like receptor 3 ligand-binding domain," Proceedings of the National Academy of Science USA, 102(31): 10976-10980 (2005).
Krug, et al., "Toll-like receptor expression reveals CpG DNA as a unique microbial stimulus for plasmacytoid dendritic cells which synergizes with CD40 ligand to induce high amounts of IL-12," European Journal of Immunology, 31: 3026-3037 (2001).
Jarrossay, et al., "Specialization and complementarity in microbial molecule recognition by human myeloid and plasmacytoid dendritic cells," European Journal of Immunology, 31: 3388-3393 (2001).
Hasan, et al., "Toll-like Receptor Signaling Stimulates Cell Cycle Entry and Progression in Fibroblasts," The Journal of Biological Chemistry, 280(21): 20620-20627 (2005).
Guillot, et al., "Involvement of Toll-like Receptor 3 in the Immune Response of Lung Epithelial Cells to Double-stranded RNA and Influenza A Virus," The Journal of Biological Chemistry, 280(7): 5571-5580 (2005).
De Bouteiller, et al., "Recognition of Double-stranded RNA by Human Toll-like Receptor 3 and Downstream Receptor Signaling Requires Multimerization and an Acidic pH," The Journal of Biological Chemistry, 280(46): 38133-38145 (2005).
Bouma, et al., "The Immunological and Genetic Basis of Inflammatory Bowel Disease," Nature Reviews Immunology, 3: 521-533 (2003).
Choe, et al., "Crystal Structure of Human Toll-Like Receptor 3 (TLR3) Ectodomain," Science, 309: 581-585 (2005).
Heil, et al., "Species-Specific Recognition of Single-Stranded RNA via Toll-like Receptor 7 and 8," Science, 303: 1526-1529 (2004).

(Continued)

*Primary Examiner*—Phillip Gambel
*Assistant Examiner*—Sharon Wen
(74) *Attorney, Agent, or Firm*—Kirk Baumeister

(57) ABSTRACT

Toll Like Receptor 3 (TLR3) modulators, such as antibodies, polynucleotides encoding TLR3 antibodies or fragments thereof, and methods of making and using the foregoing are disclosed.

3 Claims, 8 Drawing Sheets

OTHER PUBLICATIONS

Siegal, et al., "The nature of the Principal Type 1 Interferon-Producing Cells in Human Blood," Science, 284: 1835-1837 (1999).

McCullers, et al., "Lethal Synergism between Influenza Virus and *Streptococcus pneumoniae*: Characterization of a Mouse Model and the Role of Platelet-Activating Factor Receptor," The Journal of Infectious Diseases, 186: 341-350 (2002).

Kariko, et al., "mRNA Is an Endogenous Ligand for Toll-like Receptor 3," The Journal of Biological Chemistry, 279(13): 12542-12550 (2004).

Matsumoto, et al., "Establishment of a monoclonal antibody against human Toll-like receptor 3 that blocks double-stranded RNA-mediated signaling," Biochemical and Biophysical Research Communications, 293: 1364-1369 (2002).

Kariko, et al., "Suppression of RNA Recognition by Toll-like Receptors: The Impact of Nucleoside Modification and the Evolutionary Origin of RNA," Immunity, 23: 165-175 (2005).

Janeway, et al., "Innate Immune Recognition," Annual Review of Immunology, 20: 197-216 (2002).

Zipris, et al., "TLR Activation Synergizes with Kilham Rat Virus Infection to Induce Diabetes in BBDR Rats," The Journal of Immunology, 174: 131-142 (2005).

Zhou, et al., "Human Blood Dendritic Cells Selectively Express CD83, A Member of the Immunoglobulin Superfamily," The Journal of Immunology, 154: 3821-3835 (1995).

Zarember, et al., "Tissue Expression of Human Toll-Like Receptors and Differential Regulation of Toll-Like Receptor mRNAs in Leokocytes in Response to Microbes, Their Products, and Cytokines," The Journal of Immunology, 168: 554-561 (2002).

Wen, et al., "The Effect of Innate Immunity on Autoimmune Diabetes and the Expression of Toll-Like Receptors on Pancreatic Islets," The Journal of Immunology, 172: 3173-3180 (2004).

Staats, et al., "IL-1 Is an Effective Adjuvant for Mucosal and Systemic Immune Responses When Coadministered with Protein Immunogens," The Journal of Immunology, 162: 6141-6147 (1999).

Sabroe, et al., "Toll-Like Receptors in Health and Disease: Complex Questions Remain," The Journal of Immunology, 171: 1630-1635 (2003).

Kolodsick, et al., "Protection from Fluorescein Isothiocyanate-Induced Fibrosis in IL-13-Deficient, but Not IL-4 Deficient, Mice Results from Impaired Collagen Cynthesis by Fibroblasts," The Joumal of Immunology, 172: 4068-4076 (2004).

Jakubzick, et al., "Therapeutic Attenuation of Pulmonary Fibrosis Via Targeting of IL-4- and IL-13-Responsive Cells," The Journal of Immunology, 171: 2684-2693 (2003).

Hogaboam, et al., "Differential Monocyte Chemoattractant Protein-1 and Chemokine Receptor 2 Expression by Murine Lung Fibroblasts Derived from TH1- and TH2-Type Pulmonary Granuloma Models," The Journal of Immunology, 163: 2193-2201 (1999).

Hartmann, et al., "Mechanism and Function of a Newly Identified CpG DNA Motif in Human Primary B Cells," The Journal of Immunology, 164: 944-952 (2000).

Rincón, et al., "Interleukin (IL)-6 Directs the Differentiation of IL-4-producing CD4+T Cells," The Journal of Experimental Medicine, 185(3): 461-469 (1997).

Kadowaki, et al., "Subsets of Human Dendritic Cell Precursors Express Different Toll-like Receptors and Respond to Different Microbial Antigens," The Journal of Experimental Medicine, 194(6): 863-869 (2001).

Harte, et al., "The Poxvirus Protein A52R Targets Toll-like Receptor Signaling Complexes to Suppress Host Defense," The Journal of Experiental Medicine. 197(3): 343-351 (2003).

Arthur M. Krieg. "CpG Motifs in Bacterial DNA and Their Immune Effects," Annual Review of Imunology, 20: 709-760 (2002).

Guidotti, et al., "Noncytolytic Control of Viral Infections by the Innate and Adaptive Immune Response," Annual Review of Immunology, 19: 65-91 (2001).

Gross, et al., "Idiopathic Pulmonary Fibrosis," New England Journal of Medicine, 345(7): 517-525 (2001).

Medzhitov, et al., "A human homologue of the *Drosophila* Toll protein signals activation of adaptive immunity," Nature, 388: 394-397 (2000).

Douglas T. Fearon, "Seeking wisdom in innate immunity," Nature, 388: 323-324 (1997).

Rudd, et al., "Differential Role for TLR3 in Respiratory Syncytial Virus-Induced Chemokine Expression," Journal of Virology, 79(6): 3350-3357 (2005).

Donelan, et al., "The N- and C-Terminal Domains of the NS1 Protein of Influenza B Virus Can Independently Inhibit IRF-3 and Beta Interferon Promoter Activation," Journal of Virology, 78(21): 11574-11582 (2004).

Stewart, et al., "The Detection of Epstein-Barr Virus DNA in Lung Tissue from Patients with Idiopathic Pulmonary Fibrosis," American Journal of Respiratory and Critical Care Medicine, 159: 1336-1341 (1999).

Coultas, et al., "The epidemiology of interstitial lung diseases," American Journal of Respiratory and Critical Care Medicine, 150(4): 967-972 (1994).

Wong, et al., "Prophylactic and Therapeutic Efficacies of Poly(IC • LC) against Respiratory Influenza A Virus Infection in Mice," Antimicrocial Agents and Chemotherapy, 39(11): 2574-2576 (1995).

Takeda, et al., "Toll-like receptors in innate immunity," International Immunology, 17(1): 1-14 (2005).

Sun, et al., "Negative Regulation of Liver Regeneration by Innate Immunity (Natural Killer Cells/Interferon-γ)," Gastroenterology, 127: 1525-1539 (2004).

Lothar Steidler, "Microbiological and immunological strategies for treatment of inflammatory bowel disease," Microbes and Infection, 3: 1157-1166 (2001).

Rakoff-Nahoum, et al., "Recognition of Commensal Microflora by Toll-Like Receptors Is Required for Intestinal Homeostasis," Cell, 118: 229-241 (2004).

Pasare, et al., "Toll-like receptors: linking innate and adaptive immunity," Microbes and Infection, 6: 1382-1387 (2004).

Panina-Bordignon, et al., "Chemokines and their receptors in asthma and chronic obstructive pulmonary disease," Current Opinion in Pulmonary Medicine, 9(2): 104-110 (2003).

Luke AJ O'Neill, "Therapeutic targeting of Toll-like receptors fro inflammatory and infectious diseases," Current Opinion in Pharmacology, 3: 396-403 (2003).

O'Neill, et al., The Toll-IL-1 receptor adaptor family grows to five members, Trends in Immunology, 24(6): 286-289 (2003).

Pierre Miossec, "An update on the cytokine network in rheumatoid arthritis," Current Opinion in Rheumatology, 16(3): 218-222 (2004).

Joshua A. Boyce, "The role of mast cells in asthma," Prostaglandins, Leukotrienes and Essential Fatty Acids, 69: 195-205 (2003).

Manns, et al., "Peginterferon alfa-2b plus ribavirin compared with interferon alfa-2b plus ribavirin for initial treatment of chronic hepatitis C: a randomized trial," The Lancet, 358: 958-965 (2001).

Tsan, et al., "Endogenous ligands of Toll-like receptors," Journal of Leukocyte Biology, 76: 514-519 (2004).

Takeda, et al., "Microbial recognition by Toll-like receptors," Journal of Dermatological Science, 34: 73-82 (2004).

Ieki, et al., "Double-stranded RNA activates RANTES gene transcription through co-operation of nuclear factor-$_\kappa$B and interferon regulatory factors in human airway epithelial cells," Clinical and Experiental Allergy, 34: 745-752 (2004).

Hendrix, et al., "Biologic Effects After a Single Dose of Poly(I):poly($C_{12}$U) in Healthy Volunteers," Antimicrobial Agents Chemotherapy, 37(3): 429-435 (1993).

Jakubzick, et al., "Therapeutic Targeting of IL-4- and IL-13-Responsive Cells in Pulmonary Fibrosis," Immunologic Research, 30(3): 339-349 (2004).

Horner, et al., "DNA-based immunotherapeutics for the treatment of allergic disease," Immunological Reviews, 179: 102-118 (2001).

Hampe, et al., "A Genomewide Analysis Provides Evidence for Novel Linkages in Inflammatory Bowel Disease in a Large European Cohort," American Journal of Human Genetics, 64: 808-816 (1999).

Bandi, et al., "Infectious exacerbations of chronic obstructive pulmonary disease associated with respiratory viruses and non-typeable *Haemophilus influenzae*," FEMS Immunology and Medical Microbiology, 37: 69-75 (2003).

Giantonio, et al., "Toxicity and response evaluation of the interferon inducer poly ICLC administered at low dose in advanced renal carcinoma and relapsed or refractory lymphoma: A report of two clinical trials of the Eastern Cooperative Oncology Group," Investigational New Drugs, 19: 89-92 (2001).

Blair, et al., "Double-Stranded RNA-Dependent Protein Kinase Is Not Required for Double-Stranded RNA-Induced Nitric Oxide Synthase Expression or Nuclear Factor-$_κ$B Activation by Islets," Diabetes, 50: 283-290 (2001).

Sauder, et al., "Immunomodulatory and pharmacologic properties of imiquimod," Journal of American Academy of Dermatology, 43(1): S6-11 (2000).

Jakubzick, et al., "Augmented pulmonary IL-4 and IL-13 receptor subunit expression in idiopathic interstitial pneumonia," Journal of Clinical Pathology, 57: 477-486 (2004).

Liu, et al., "Double-Stranded RNA Cooperates with Interferon-γand IL-1β to Induce Both Chemokine Expression and Nuclear Factor-$_κ$B-Dependent Apoptosis in Pancreatic β-Cells: Potential Mechanisms for Viral-Induced Insulitis and β-Cell Death in Type 1 Diabetes Mellitus," Endocrinology, 143(4): 1225-1234 (2002).

F.Q.B. Alenzi, "Links between apoptosis, proliferation and the Cell cycle," British Journal of Biomedical Science, 61(2): 99-102 (2004).

Okayasu, et al., "A Novel Method in the Induction of Reliable Experimental Acute and Chronic Ulcerative Colitis in Mice," Gastroenterology, 98: 694-702 (1990).

Andreakos, et al., "Is targeting Toll-like receptors and their signaling pathway a useful therapeutic approach to modulating cytokine-driven inflammation?" Immunological Reviews, 202: 250-265 (2004).

Coultas. et al., "The Epidemiology of Interstitial Lung Disease," American Journal of Respiratory and Critical Care Medicine, 150: 967-972 (1994).

Sebastian L. Johnston, "Natural and Experimental Rhinovirus Infections of the Lower Respiratory Tract," American Journal of Respiratory and Critical Care Medicine, 152: S46-S52 (1995).

Tang, et al., "Herpesvirus DNA Is Consistently Detected in Lungs of Patients with Idiopathic Pulmonary Fibrosis," Journal of Clinical Microbiology, 41(6): 2633-2640 (2003).

Cario, et al., "Differential Alteration in Intestinal Epithelial Cell Expression of Toll-Like Receptor 3 (TLR3) and TLR4 in Inflammatory Bowel Disease," Infetion and Immunity, 68(12): 7010-7017 (2000).

Hancock, et al., "Production of Interleukin 13 by Alveolar Macrophages front Normal and Fibrotic Lung," American Journal of Respiratory and Cell Molecular Biology, 18: 60-65 (1998).

Belperio, et al., "Interaction of IL-13 and C10 in the Pathogenesis of Bleomycin-Induced Pulmonary Fibrosis," American Journal of Respiratory and Cell Molecular Biology, 27: 419-417 (2002).

Gern, et al., "Double-Stranded RNA Induces the Synthesis of Specific Chemokines by Bronchial Epithelial Cells," American Journal of Respiratory and Cell Molecular Biology, 28: 731-737 (2003).

Sha, et al., "Activation of Airway Epithelial Cells by Toll-Like Receptor Agonists," American Journal of Respiratory and Cell Molecular Biology, 31: 358-364 (2004).

Charles E. Samuel, "Antiviral Actions of Interferons," Clinical Microbiology Reviews, 14(4), 778-809 (2001).

Hendrickson, et al., "Clinical Aspects and Pathophysiology of Inflammatory Bowel Disease," Clinical Microbiology Reviews, 15(1): 79-94 (2002).

Van Amersfoort, et al., Receptors, Mediators, and Mechanisms Involved in Bacterial Sepsis and Septic Shock, Clinical Microbiology Reviews, 16(3): 379-414 (2003).

Ayala, et al, "Mechanisms of immune resolution," Critical Care Medicine, 31(8): S558-S571 (2003).

Akira, et al., "Toll-like Receptors and Innate Immunity," Advances in Immunology, 78: 1-56 (2001).

Stark, et al, "How Cells Respond to Interferons," Annual Reviews in Biochemistry, 67: 227-264 (1998).

Ogata, et al., "Cytokine and Anti-cytokine Therapies for Inflammatory Bowel Disease," Current Pharmaceutical Design, 9: 1107-1113 (2003).

Medzhitov, et al., "Innate immune recognition: mechanisms and pathways," Immunological Reviews, 173: 89-97 (2000).

Sartor, et al., "Current Concepts of the Etiology and Pathogenesis of Ulcerative Colitis and Crohn's Disease," Gastroenterology Clinics of North America, 24(3): 475-507 (1995).

Schetter, et al, "Toll-like receptors involved in the response to microbial pathogens: Development of agonists for toll-like receptor 9,"Current Opinion in Drug Discovery & Development, 7(2): 204-210 (2004).

Lok, et al, "Viruses and idiopathic pulmonary fibrosis," Monaldi Archives of Chest Disease, 55(2): 146-150 (2000).

Shaun, et at., "Chemokines and dendritic cells: A crucial alliance," Immunology and Cell Biology, 80: 489-496 (2002).

Bhattacharjee, et al., "Toll-Like Receptor Signaling: Emerging Opportunities in Human Diseases and Medicine," Current Immunology Reviews, 1(1): 81-90 (2005).

PCT International Search Report dated Sep. 26, 2007.

\* cited by examiner

Figure 1

Nucleotide sequence for C1130 heavy chain variable region
ATGGAATGTAACTGGATACTTCCTTTTATTCTGTCGGTAATTTCAGGGGTCTACTCAGAGGTTCA
GCTCCAGCAGTCTGGGACTGTGCTGGCAAGGCCTGGGGCTTCCGTGAAGATGTCCTGCAAGGCTT
CTGGCTACAGGTTTTCCAGCTACGGGATGCACTGGGTAAAACAGAGGCCTGGACAGGGTCTAGAA
TGGATTGGTGCTATTTATCCTGGAAACAATGATATTACTTATACTCAGAAGTTCAAGGGCAAGGC
CAAACTGACTGCAGTCACATCCGCCAGCACTACCTACATGGAACTCAGCAGCCTGACAAATGAAG
ACTCTGCGGTCTATTACTGTTCAACTCTAATGTTTGCTTATTGGGGCCAAGGGACTCTGGTCACT
GTCACTGCA    (SEQ ID NO: 5)

Amino Acid sequence for C1130 Heavy Chain variable region
MECNWILPFILSVISGVYSEVQLQQSGTVLARPGASVKMSCKASGYRFSSYGMHWVKQRPGQGLE
WIGAIYPGNNDITYTQKFKGKAKLTAVTSASTTYMELSSLTNEDSAVYYCSTLMFAYWGQGTLVT
VTA    (SEQ ID NO: 6)

Signal Sequence
MECNWILPFILSVISGVYS    (SEQ ID NO: 7)

FR1
EVQLQQSGTVLARPGASVKMSCKAS    (SEQ ID NO: 8)

CDR1
GYRFSSYGMH    (SEQ ID NO: 9)

FR2
WVKQRPGQGLEWIG    (SEQ ID NO: 10)

CDR2
AIYPGNNDITYTQKFKG    (SEQ ID NO: 11)

FR3
KAKLTAVTSASTTYMELSSLTNEDSAVYYCST    (SEQ ID NO: 12)

CDR3
LMFAY    (SEQ ID NO: 13)

Mouse J HC
WGQGTLVTVTA    (SEQ ID NO: 14)

Figure 2

Nucleotide sequence for C1130 Light Chain variable region
ATGGACATGAGGGTTCCTGCTCACGTTTTTGGCTTCTTGTTGCTCTGGTTTCCAGGTACCAGATG
TGACATCCAGATGACCCAGTCTCCATCTTCCTTATCTGCCTCTCTGGGAGAAAGAGTCAGTCTCA
CTTGTCGGGCAAGTCAGGAAATTAGTGATCACTTAAGTTGGCTTCAGCAGAAATCGGGTGGAACT
ATTAAACGCCTGGTCTATGCCGCATCCACTTTAGATTCTGGTGTCCCAAAAAGGTTCAGTGGCAG
TAGGTCTGGGTCAGACTTTTCTCTCACCATCAGCAGCCTTGAGTCTGAAGATTTTGCAGACTATT
ACTGTCTACGATATGATAATTATCCGTGGACGTTCGGTGCAGGCACCAGGCTGGAAATCAGA
(SEQ ID NO: 15)

Amino Acid sequence for C1130 Light Chain variable region
MDMRVPAHVFGFLLLWFPGTRCDIQMTQSPSSLSASLGERVSLTCRASQEISDHLSWLQQKSGGT
IKRLVYAASTLDSGVPKRFSGSRSGSDFSLTISSLESEDFADYYCLRYDNYPWTFGAGTRLEIR
(SEQ ID NO: 16)

Signal sequence
MDMRVPAHVFGFLLLWFPGTRC   (SEQ ID NO: 17)

FR1
DIQMTQSPSSLSASLGERVSLTC   (SEQ ID NO: 18)

CDR1
RASQEISDHLS   (SEQ ID NO: 19)

FR2
WLQQKSGGTIKRLVY   (SEQ ID NO: 20)

CDR2
AASTLDS   (SEQ ID NO: 21)

FR3
GVPKRFSGSRSGSDFSLTISSLESEDFADYYC   (SEQ ID NO: 22)

CDR3
LRYDNYPWT   (SEQ ID NO: 23)

Mouse J KAPPA
FGAGTRLEIR   (SEQ ID NO: 24)

293-TLR3

A549-TLR3.2

SEQUENCE LISTING

<160> NUMBER OF SEQ ID NOS: 24

<210> SEQ ID NO 1
<211> LENGTH: 2712
<212> TYPE: DNA
<213> ORGANISM: Homo sapiens

<400> SEQUENCE: 1

| | | | | | |
|---|---|---|---|---|---|
| atgagacaga | ctttgccttg | tatctacttt | tgggggggcc | ttttgccctt | tgggatgctg | 60 |
| tgtgcatcct | ccaccaccaa | gtgcactgtt | agccatgaag | ttgctgactg | cagccacctg | 120 |
| aagttgactc | aggtacccga | tgatctaccc | acaaacataa | cagtgttgaa | ccttacccat | 180 |
| aatcaactca | gaagattacc | agccgccaac | ttcacaaggt | atagccagct | aactagcttg | 240 |
| gatgtaggat | taacaccat | ctcaaaactg | gagccagaat | tgtgccagaa | acttcccatg | 300 |
| ttaaaagttt | tgaacctcca | gcacaatgag | ctatctcaac | tttctgataa | aacctttgcc | 360 |
| ttctgcacga | atttgactga | actccatctc | atgtccaact | caatccagaa | aattaaaaat | 420 |
| aatcccttg | tcaagcagaa | gaatttaatc | acattagatc | tgtctcataa | tggcttgtca | 480 |
| tctacaaaat | taggaactca | ggttcagctg | gaaaatctcc | aagagcttct | attatcaaac | 540 |
| aataaaattc | aagcgctaaa | aagtgaagaa | ctggatatct | ttgccaattc | atctttaaaa | 600 |
| aaattagagt | tgtcatcgaa | tcaaattaaa | gagttttctc | cagggtgttt | tcacgcaatt | 660 |
| ggaagattat | ttggcctctt | tctgaacaat | gtccagctgg | gtcccagcct | tacagagaag | 720 |
| ctatgtttgg | aattagcaaa | cacaagcatt | cggaatctgt | ctctgagtaa | cagccagctg | 780 |
| tccaccacca | gcaatacaac | tttcttggga | ctaaagtgga | caaatctcac | tatgctcgat | 840 |
| ctttcctaca | caaacttaaa | tgtggttggt | aacgattcct | ttgcttggct | tccacaacta | 900 |
| gaatatttct | tcctagagta | taataatata | cagcatttgt | tttctcactc | tttgcacggg | 960 |
| cttttcaatg | tgaggtacct | gaatttgaaa | cggtctttta | ctaaacaaag | tatttccctt | 1020 |
| gcctcactcc | ccaagattga | tgatttttct | tttcagtggc | taaaatgttt | ggagcacctt | 1080 |
| aacatggaag | ataatgatat | tccaggcata | aaaagcaata | tgttcacagg | attgataaac | 1140 |
| ctgaaatact | taagtctatc | caactccttt | acaagtttgc | gaactttgac | aaatgaaaca | 1200 |
| tttgtatcac | ttgctcattc | tccttacac | atactcaacc | taaccaagaa | taaaatctca | 1260 |
| aaaatagaga | gtgatgcttt | ctcttggttg | ggccacctag | aagtacttga | cctgggcctt | 1320 |
| aatgaaattg | ggcaagaact | cacaggccag | gaatggagag | gtctagaaaa | tattttcgaa | 1380 |
| atctatcttt | cctacaacaa | gtacctgcag | ctgactagga | actcctttgc | cttggtccca | 1440 |
| agccttcaac | gactgatgct | ccgaagggtg | gcccttaaaa | atgtggatag | ctctcccttca | 1500 |

-continued

```
ccattccagc ctcttcgtaa cttgaccatt ctggatctaa gcaacaacaa catagccaac    1560
ataaatgatg acatgttgga gggtcttgag aaactagaaa ttctcgattt gcagcataac    1620
aacttagcac ggctctggaa acacgcaaac cctggtggtc ccatttattt cctaaagggt    1680
ctgtctcacc tccacatcct taacttggag tccaacggct tgacgagat cccagttgag     1740 gtcttcaagg atttatttga actaaagatc atcgatttag gattgaataa tttaaacaca    1800
cttccagcat ctgtctttaa taatcaggtg tctctaaagt cattgaacct tcagaagaat    1860
ctcataacat ccgttgagaa gaaggttttc gggccagctt tcaggaacct gactgagtta    1920
gatatgcgct ttaatcccct tgattgcacg tgtgaaagta ttgcctggtt tgttaattgg    1980
attaacgaga cccataccaa catccctgag ctgtcaagcc actacctttg caacactcca    2040
cctcactatc atgggttccc agtgagactt tttgatacat catcttgcaa agacagtgcc    2100 cccctttgaac tcttttcat gatcaatacc agtatcctgt tgatttttat ctttattgta    2160
cttctcatcc actttgaggg ctggaggata tcttttttatt ggaatgtttc agtacatcga    2220
gttcttggtt tcaaagaaat agacagacag acagaacagt ttgaatatgc agcatatata    2280
attcatgcct ataagataa ggattgggtc tgggaacatt tctcttcaat ggaaaaggaa     2340
gaccaatctc tcaaattttg tctggaagaa agggactttg aggcgggtgt ttttgaacta    2400
gaagcaattg ttaacagcat caaaagaagc agaaaaatta ttttttgttat aacacaccat   2460 ctattaaaag acccattatg caaaagattc aaggtacatc atgcagttca acaagctatt    2520
gaacaaaatc tggattccat tatattggtt ttccttgagg agattccaga ttataaactg    2580
aaccatgcac tctgtttgcg aagaggaatg tttaaatctc actgcatctt gaactggcca    2640
gttcagaaag aacggatagg tgcctttcgt cataaattgc aagtagcact tggatccaaa    2700
aactctgtac at                                                        2712
```

<210> SEQ ID NO 2
<211> LENGTH: 904
<212> TYPE: PRT
<213> ORGANISM: Homo sapiens

<400> SEQUENCE: 2

```
Met Arg Gln Thr Leu Pro Cys Ile Tyr Phe Trp Gly Gly Leu Leu Pro
 1               5                  10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
 65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160
```

```
Ser Thr Lys Leu Gly Thr Gln Val Gln Leu Glu Asn Leu Gln Glu Leu
            165                 170                 175

Leu Leu Ser Asn Asn Lys Ile Gln Ala Leu Lys Ser Glu Glu Leu Asp
        180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575
```

-continued

```
Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
    690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 3
<211> LENGTH: 2109
<212> TYPE: DNA
<213> ORGANISM: Homo sapiens

<400> SEQUENCE: 3
atgagacaga ctttgccttg tatctacttt tggggggggcc ttttgccctt tgggatgctg      60
tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
```

```
gatgtaggat ttaacaccat ctcaaaactg gagccagaat tgtgccagaa acttcccatg    300
ttaaaagttt tgaacctcca gcacaatgag ctatctcaac tttctgataa aacctttgcc    360
ttctgcacga atttgactga actccatctc atgtccaact caatccagaa aattaaaaat    420
aatccctttg tcaagcagaa gaatttaatc acattagatc tgtctcataa tggcttgtca    480
tctacaaaat taggaactca ggttcagctg gaaaatctcc aagagcttct attatcaaac    540
aataaaattc aagcgctaaa aagtgaagaa ctggatatct ttgccaattc atctttaaaa    600
aaattagagt tgtcatcgaa tcaaattaaa gagttttctc agggtgtttt tcacgcaatt    660
ggaagattat ttggcctctt tctgaacaat gtccagctgg gtcccagcct acagagaag    720 ctatgtttgg aattagcaaa cacaagcatt cggaatctgt ctctgagtaa cagccagctg    780
tccaccacca gcaatacaac tttcttggga ctaaagtgga caaatctcac tatgctcgat    840 cttttcctaca caacttaaa tgtggttggt aacgattcct ttgcttggct tccacaacta    900
gaatatttct tcctagagta taataatata cagcatttgt tttctcactc tttgcacggg    960
cttttcaatg tgaggtacct gaatttgaaa cggtctttta ctaaacaaag tatttcccctt   1020 gcctcactcc ccaagattga tgattttct tttcagtggc taaatgtttt ggagcacctt   1080
aacatggaag ataatgatat tccaggcata aaaagcaata tgttcacagg attgataaac   1140
ctgaaatact taagtctatc caactccttt acaagtttgc gaactttgac aaatgaaaca   1200
tttgtatcac ttgctcattc tcccttacac atactcaacc taaccaagaa taaaatctca   1260
aaaatagaga gtgatgcttt ctcttggttg ggccacctag aagtacttga cctgggcctt   1320
aatgaaattg ggcaagaact cacaggccag gaatggagag gtctagaaaa tatttttcgaa  1380 atctatcttt cctacaacaa gtacctgcag ctgactagga actcctttgc cttggtccca   1440
agccttcaac gactgatgct ccgaagggtg gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct tgacgagat cccagttgag   1740 gtcttcaagg attatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggttttc gggccagctt tcaggaacct gactgagtta   1920
gatatgcgct ttaatcccct tgattgcacg tgtgaaagta ttgcctggtt tgttaattgg   1980
attaacgaga cccataccaa catccctgag ctgtcaagcc actacccttg caacactcca   2040
cctcactatc atgggttccc agtgagactt tttgatacat catcttgcaa agacagtgcc   2100
cccttttgaa                                                          2109
```

<210> SEQ ID NO 4
<211> LENGTH: 703
<212> TYPE: PRT
<213> ORGANISM: Homo sapiens

<400> SEQUENCE: 4

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp

```
                35                  40                  45
Leu Pro Thr Asn Ile Thr Val Leu Asn Leu Thr His Asn Gln Leu Arg
 50                  55                  60

Arg Leu Pro Ala Ala Asn Phe Thr Arg Tyr Ser Gln Leu Thr Ser Leu
 65                  70                  75                  80

Asp Val Gly Phe Asn Thr Ile Ser Lys Leu Glu Pro Glu Leu Cys Gln
                 85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
                115                 120                 125

His Leu Met Ser Asn Ser Ile Gln Lys Ile Lys Asn Asn Pro Phe Val
                130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
                180                 185                 190

Ile Phe Ala Asn Ser Ser Leu Lys Lys Leu Glu Leu Ser Ser Asn Gln
                195                 200                 205

Ile Lys Glu Phe Ser Pro Gly Cys Phe His Ala Ile Gly Arg Leu Phe
                210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
                260                 265                 270

Trp Thr Asn Leu Thr Met Leu Asp Leu Ser Tyr Asn Asn Leu Asn Val
                275                 280                 285

Val Gly Asn Asp Ser Phe Ala Trp Leu Pro Gln Leu Glu Tyr Phe Phe
290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
                340                 345                 350

Trp Leu Lys Cys Leu Glu His Leu Asn Met Glu Asp Asn Asp Ile Pro
                355                 360                 365

Gly Ile Lys Ser Asn Met Phe Thr Gly Leu Ile Asn Leu Lys Tyr Leu
                370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
                420                 425                 430

Leu Glu Val Leu Asp Leu Gly Leu Asn Glu Ile Gly Gln Glu Leu Thr
                435                 440                 445

Gly Gln Glu Trp Arg Gly Leu Glu Asn Ile Phe Glu Ile Tyr Leu Ser
                450                 455                 460
```

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
        500                 505                 510

Leu Ser Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
        530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu
    690                 695                 700

<210> SEQ ID NO 5
<211> LENGTH: 399
<212> TYPE: DNA
<213> ORGANISM: Mus musculus

<400> SEQUENCE: 5
atggaatgta actgatatact tccttttatt ctgtcggtaa tttcagggggt ctactcagag      60 gttcagctcc agcagtctgg gactgtgctg gcaaggcctg ggcttccgt gaagatgtcc       120 tgcaaggctt ctggctacag gttttccagc tacgggatgc actgggtaaa acagaggcct      180
ggacagggtc tagaatggat tggtgctatt tatcctggaa acaatgatat tacttatact      240
cagaagttca gggcaaggc caaactgact gcagtcacat ccgccagcac tacctacatg       300
gaactcagca gcctgacaaa tgaagactct gcggtctatt actgttcaac tctaatgttt       360
gcttattggg gccaagggac tctggtcact gtcactgca                             399

<210> SEQ ID NO 6
<211> LENGTH: 133
<212> TYPE: PRT
<213> ORGANISM: Mus musculus

<400> SEQUENCE: 6

Met Glu Cys Asn Trp Ile Leu Pro Phe Ile Leu Ser Val Ile Ser Gly
1               5                   10                  15

-continued

Val Tyr Ser Glu Val Gln Leu Gln Gln Ser Gly Thr Val Leu Ala Arg
         20                  25                  30

Pro Gly Ala Ser Val Lys Met Ser Cys Lys Ala Ser Gly Tyr Arg Phe
         35                  40                  45

Ser Ser Tyr Gly Met His Trp Val Lys Gln Arg Pro Gly Gln Gly Leu
     50                  55                  60

Glu Trp Ile Gly Ala Ile Tyr Pro Gly Asn Asn Asp Ile Thr Tyr Thr
 65                  70                  75                  80

Gln Lys Phe Lys Gly Lys Ala Lys Leu Thr Ala Val Thr Ser Ala Ser
                 85                  90                  95

Thr Thr Tyr Met Glu Leu Ser Ser Leu Thr Asn Glu Asp Ser Ala Val
                100                 105                 110

Tyr Tyr Cys Ser Thr Leu Met Phe Ala Tyr Trp Gly Gln Gly Thr Leu
            115                 120                 125

Val Thr Val Thr Ala
        130

<210> SEQ ID NO 7
<211> LENGTH: 19
<212> TYPE: PRT
<213> ORGANISM: Mus musculus

<400> SEQUENCE: 7

Met Glu Cys Asn Trp Ile Leu Pro Phe Ile Leu Ser Val Ile Ser Gly
 1               5                  10                  15

Val Tyr Ser

<210> SEQ ID NO 8
<211> LENGTH: 25
<212> TYPE: PRT
<213> ORGANISM: Mus musculus

<400> SEQUENCE: 8

Glu Val Gln Leu Gln Gln Ser Gly Thr Val Leu Ala Arg Pro Gly Ala
 1               5                  10                  15

Ser Val Lys Met Ser Cys Lys Ala Ser
             20                  25

<210> SEQ ID NO 9
<211> LENGTH: 10
<212> TYPE: PRT
<213> ORGANISM: Mus musculus

<400> SEQUENCE: 9

Gly Tyr Arg Phe Ser Ser Tyr Gly Met His
 1               5                  10

<210> SEQ ID NO 10
<211> LENGTH: 14
<212> TYPE: PRT
<213> ORGANISM: Mus musculus

<400> SEQUENCE: 10

Trp Val Lys Gln Arg Pro Gly Gln Gly Leu Glu Trp Ile Gly
 1               5                  10

<210> SEQ ID NO 11
<211> LENGTH: 17
<212> TYPE: PRT
<213> ORGANISM: Mus musculus

<400> SEQUENCE: 11

Ala Ile Tyr Pro Gly Asn Asn Asp Ile Thr Tyr Thr Gln Lys Phe Lys
1               5                   10                  15
Gly

<210> SEQ ID NO 12
<211> LENGTH: 32
<212> TYPE: PRT
<213> ORGANISM: Mus musculus

<400> SEQUENCE: 12

Lys Ala Lys Leu Thr Ala Val Thr Ser Ala Ser Thr Thr Tyr Met Glu
1               5                   10                  15

Leu Ser Ser Leu Thr Asn Glu Asp Ser Ala Val Tyr Tyr Cys Ser Thr
            20                  25                  30

<210> SEQ ID NO 13
<211> LENGTH: 5
<212> TYPE: PRT
<213> ORGANISM: Mus musculus

<400> SEQUENCE: 13

Leu Met Phe Ala Tyr
1               5

<210> SEQ ID NO 14
<211> LENGTH: 11
<212> TYPE: PRT
<213> ORGANISM: Mus musculus

<400> SEQUENCE: 14

Trp Gly Gln Gly Thr Leu Val Thr Val Thr Ala
1               5                   10

<210> SEQ ID NO 15
<211> LENGTH: 387
<212> TYPE: DNA
<213> ORGANISM: Mus musculus

<400> SEQUENCE: 15
atggacatga gggttcctgc tcacgttttt ggcttcttgt tgctctggtt tccaggtacc      60
agatgtgaca tccagatgac ccagtctcca tcttccttat ctgcctctct gggagaaaga     120
gtcagtctca cttgtcgggc aagtcaggaa attagtgatc acttaagttg gcttcagcag     180
aaatcgggtg aactattaa cgcctggtc tatgccgcat ccactttaga ttctggtgtc      240
ccaaaaaggt tcagtggcag taggtctggg tcagactttt ctctcaccat cagcagcctt     300
gagtctgaag attttgcaga ctattactgt ctacgatatg ataattatcc gtggacgttc     360
ggtgcaggca ccaggctgga aatcaga                                        387

<210> SEQ ID NO 16
<211> LENGTH: 129
<212> TYPE: PRT
<213> ORGANISM: Mus musculus

<400> SEQUENCE: 16

Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

-continued

```
Leu Ser Ala Ser Leu Gly Glu Arg Val Ser Leu Thr Cys Arg Ala Ser
            35                  40                  45

Gln Glu Ile Ser Asp His Leu Ser Trp Leu Gln Gln Lys Ser Gly Gly
        50                  55                  60

Thr Ile Lys Arg Leu Val Tyr Ala Ala Ser Thr Leu Asp Ser Gly Val
 65                  70                  75                  80

Pro Lys Arg Phe Ser Gly Ser Arg Ser Gly Ser Asp Phe Ser Leu Thr
                85                  90                  95

Ile Ser Ser Leu Glu Ser Glu Asp Phe Ala Asp Tyr Tyr Cys Leu Arg
            100                 105                 110

Tyr Asp Asn Tyr Pro Trp Thr Phe Gly Ala Gly Thr Arg Leu Glu Ile
            115                 120                 125

Arg

<210> SEQ ID NO 17
<211> LENGTH: 22
<212> TYPE: PRT
<213> ORGANISM: Mus musculus

<400> SEQUENCE: 17

Met Asp Met Arg Val Pro Ala His Val Phe Gly Phe Leu Leu Leu Trp
 1               5                  10                  15

Phe Pro Gly Thr Arg Cys
            20

<210> SEQ ID NO 18
<211> LENGTH: 23
<212> TYPE: PRT
<213> ORGANISM: Mus musculus

<400> SEQUENCE: 18

Asp Ile Gln Met Thr Gln Ser Pro Ser Ser Leu Ser Ala Ser Leu Gly
 1               5                  10                  15

Glu Arg Val Ser Leu Thr Cys
            20

<210> SEQ ID NO 19
<211> LENGTH: 11
<212> TYPE: PRT
<213> ORGANISM: Mus musculus

<400> SEQUENCE: 19

Arg Ala Ser Gln Glu Ile Ser Asp His Leu Ser
 1               5                  10

<210> SEQ ID NO 20
<211> LENGTH: 15
<212> TYPE: PRT
<213> ORGANISM: Mus musculus

<400> SEQUENCE: 20

Trp Leu Gln Gln Lys Ser Gly Gly Thr Ile Lys Arg Leu Val Tyr
 1               5                  10                  15

<210> SEQ ID NO 21
<211> LENGTH: 7
<212> TYPE: PRT
<213> ORGANISM: Mus musculus

<400> SEQUENCE: 21

Ala Ala Ser Thr Leu Asp Ser
```

-continued

```
<210> SEQ ID NO 22
<211> LENGTH: 32
<212> TYPE: PRT
<213> ORGANISM: Mus musculus

<400> SEQUENCE: 22

Gly Val Pro Lys Arg Phe Ser Gly Ser Arg Ser Gly Ser Asp Phe Ser
 1               5                  10                  15

Leu Thr Ile Ser Ser Leu Glu Ser Glu Asp Phe Ala Asp Tyr Tyr Cys
             20                  25                  30

<210> SEQ ID NO 23
<211> LENGTH: 9
<212> TYPE: PRT
<213> ORGANISM: Mus musculus

<400> SEQUENCE: 23

Leu Arg Tyr Asp Asn Tyr Pro Trp Thr
 1               5

<210> SEQ ID NO 24
<211> LENGTH: 10
<212> TYPE: PRT
<213> ORGANISM: Mus musculus

<400> SEQUENCE: 24

Phe Gly Ala Gly Thr Arg Leu Glu Ile Arg
 1               5                  10
```

ANTIBODY REACTIVE WITH HUMAN TOLL LIKE RECEPTOR 3

CROSS-REFERENCE TO RELATED APPLICATION

This application claims the benefit of U.S. Provisional Application Ser. No. 60/730,793, filed 27 Oct. 2005, the entire contents of which is incorporated herein by reference.

FIELD OF THE INVENTION

The present invention relates to Toll Like Receptor 3 (TLR3) modulators such as antibodies.

BACKGROUND OF THE INVENTION

Recognition of foreign antigens by mammalian cells can be mediated by a set of innate immune receptors called Toll-like receptors (TLRs). TLRs recognize conserved patterns derived from microbial pathogens identified as pathogen-associated molecular patterns (PAMPs) (Barton et al., *Science* 300:1524-1525, 2003). Interaction of a TLR with a PAMP results in a signaling cascade involving NF-κB activation and transcription of cytokine gene expression. Ten human toll-like receptors and five TLR adaptor proteins have been identified.

TLRs are able to expand their repertoire of ligands by forming homo- or heterodimers as well as binding different adaptor proteins. For example, TLR3 binds dsRNA, an intermediate in viral replication. TLR3 also interacts with PolyI:C, a synthetic dsRNA analog, and mRNA from necrotic cells. Activation of TLR3 leads to the secretion of Type I interferons, which are important in the control of viral infection. A full-length human TLR3 amino acid sequence and encoding polynucleotide sequence are shown in SEQ ID NOs: 1 and 2, respectively. TLRs TLR7, TLR8, and TLR9 also have nucleic acid ligands; activation of these TLRs can also lead to interferon secretion.

Type I interferons trigger signaling cascades to activate a set of immediate early-response genes (IFN-stimulated genes or ISGs) and have proven useful in the clinic. The resulting antiviral activities include mRNA translation inhibition, RNA editing, and RNA degradation (Samuel et al., *Clin Microbiol Rev* 14:778-809, 2001). Currently, a combination therapy of pegylated interferon and the broad-spectrum antiviral compound ribavirin is being used to treat hepatitis C infection (Manns et al., *Lancet* 358:958-965, 2001).

The critical anti-viral role of Type I IFNs is further demonstrated by the evolution of viral resistance mechanisms to inhibit the production of Type I IFNs by infected host cells. For example, the NS1 protein of influenza antagonizes IRF-3 activation and IFNβ production (Donelan et al., *J Virol* 78: 11574-11582, 2004) and the A52R poxvirus protein associates with IRAK2 and TRAF6 to block signaling downstream of TLR3 (Harte et al., *J Exp Med*, 197:343-351, 2003). Thus, therapies based on triggering TLR activation or enhancing TLR-mediated signaling pathways increase endogenous IFNα/β production and assist the host in the control of acute viral infections.

The use of TLR agonists to modulate the outcome of an immune response is currently being investigated for therapeutic use (O'Neill, *Curr Opin Pharm* 3:396-403, 2003; Schetter et al., *Curr Opin Drug Discov Devel* 7:204-210, 2004). For example, CpG oligodinucleotides (ODN), a TLR9 ligand, are capable of stimulating the production of type I IFN and a $T_E1$ response (Krieg, *Annu Rev Immunol* 20:709-60, 2002), a finding that suggests the possible use of CpG ODN not only as a vaccine adjuvant but also for the treatment and or prevention of diseases that necessitate a potent $T_H1$ response. Another example is the synthetic TLR7 agonist imiquimod, an approved agent for the treatment of genital warts; its protective effect is thought to be mediated through the stimulation of inflammatory cytokines such as IFNα, TNFα and IL-1β (Saunder, *J Amer Acad Derm* 43: S6-S11, 2000). Overall, these findings show that TLR agonists are a novel class of immunomodulatory agents with the potential of having a significant therapeutic benefit.

Thus, a need exists for the identification of novel immunomodulatory agents that potentiate the effect of TLR agonists. Such novel TLR-based therapies are expected to have an advantage of providing a sustained immune response with less frequent dosing regimens.

BRIEF DESCRIPTION OF THE DRAWINGS

FIG. 1 shows C1130 anti-hTLR3 mAb heavy chain variable region sequences.

FIG. 2 shows C1130 anti-hTLR3 mAb light chain variable region sequences.

SUMMARY OF THE INVENTION

Figure 3:
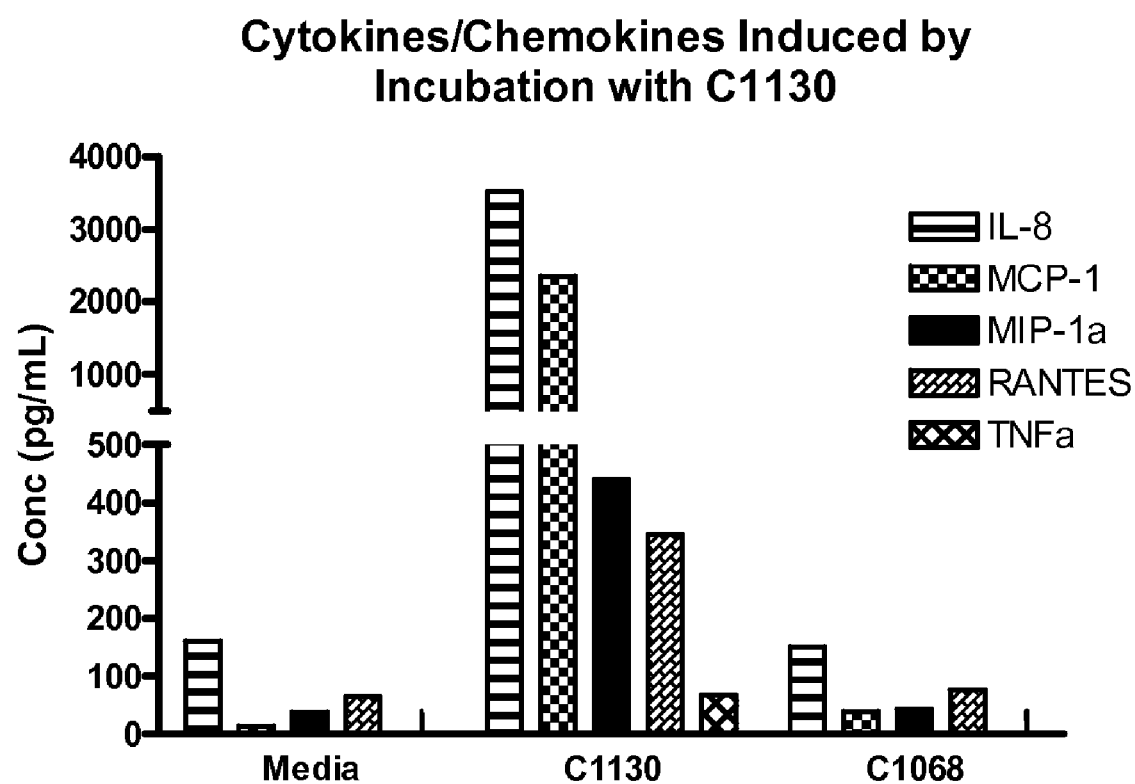
FIG. 3 shows C1130 induced IL-8, MCP-1, MIP-1α, RANTES, and TNFα secretion by human peripheral blood mononuclear cells (PBMCs) at 24 h.

One aspect of the invention is an isolated antibody reactive with human Toll Like Receptor 3 (hTLR3) or its homologs that induces cellular production of a cytokine selected from the group consisting of IL-8, MCP-1, MIP1-α, RANTES and TNF-α.

Another aspect of the invention is an isolated antibody reactive with hTLR3 or its homologs that modifies an immune response to other Toll Like Receptor ligands.

Another aspect of the invention is an isolated antibody reactive with hTLR3 having the antigen binding ability of a monoclonal antibody comprising the amino acid sequences of the heavy chain complementarity determining regions (CDRs) as shown in SEQ ID NOs: 9, 11 and 13 and the amino acid sequences of the light chain CDRs as shown in SEQ ID NOs: 19, 21 and 23.

Another aspect of the invention is an isolated antibody reactive with hTLR3 comprising the amino acid sequences of the heavy chain complementarity determining regions (CDRs) as shown in SEQ ID NOs: 9, 11 and 13 and the amino acid sequences of the light chain CDRs as shown in SEQ ID NOs: 19, 21 and 23.

Another aspect of the invention is an isolated antibody reactive with hTLR3 comprising a heavy chain comprising the amino acid sequence shown in SEQ ID NO: 6 and a light chain comprising the amino acid sequence shown in SEQ ID NO: 16.

Another aspect of the invention is an isolated polynucleotide encoding an antibody heavy chain comprising the CDR amino acid sequences shown in SEQ ID NOs: 9, 11 and 13.

Another aspect of the invention is an isolated polynucleotide encoding an antibody light chain comprising the CDR amino acid sequences shown in SEQ ID NOs: 19, 21 and 23.

Another aspect of the invention is an isolated polynucleotide encoding an antibody heavy chain comprising the amino acid sequence shown in SEQ ID NO: 6.

Another aspect of the invention is an isolated polynucleotide encoding an antibody light chain comprising the amino acid sequence shown in SEQ ID NO: 16.

Other aspects of the invention include methods of treating or preventing viral infection comprising administering to a patient a therapeutically effective amount of an antibody of the invention in combination with an immune stimulant.

Another aspect of the invention is a method of treating cancer comprising administering to a patient a therapeutically effective amount of an antibody of the invention in combination with an immune stimulant.

Another aspect of the invention is a method of treating inflammatory bowel disease comprising administering to a patient a therapeutically effective amount of an antibody of the invention in combination with an immune stimulant.

Other aspects of the invention include methods of treating or preventing a viral infection-associated symptom comprising administering to a patient a therapeutically effective amount of an antibody of the invention in combination with a Toll-Like Receptor 7 (TLR7) agonist.

Other aspects of the invention include methods of treating or preventing a pulmonary disease and pathogen-mediated exacerbation comprising administering to a patient a therapeutically effective amount of an antibody of the invention in combination with a TLR9 or TLR7 agonist.

Other aspects of the invention include methods of treating or preventing graft-versus-host disease (GVHD) comprising administering to a patient a therapeutically effective amount of an antibody of the invention in combination with a TLR9 or TLR7 agonist.

Other aspects of the invention include methods of treating or preventing autoimmune disease comprising administering to a patient a therapeutically effective amount of an antibody of the invention in combination with an immune treatment.

DETAILED DESCRIPTION OF THE INVENTION

All publications, including but not limited to patents and patent applications, cited in this specification are herein incorporated by reference as though fully set forth.

The term "antibodies" as used herein is meant in a broad sense and includes immunoglobulin or antibody molecules including polyclonal antibodies, monoclonal antibodies including murine, human, humanized and chimeric monoclonal antibodies and antibody fragments.

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragments" means a portion of an intact antibody, generally the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies.

The term "antigen" as used herein means any molecule that has the ability to generate antibodies either directly or indirectly. Included within the definition of "antigen" is a protein-encoding nucleic acid.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The term "homolog" means protein sequences having between 40% and 100% sequence identity to a reference sequence. Homologs of hTLR3 include polypeptides from other species that have between 40% and 100% sequence identity to a known hTLR3 sequence. Percent identity between two peptide chains can be determined by pair wise alignment using the default settings of the AlignX module of Vector NTI v.9.0.0 (Invitrogen Corp., Carslbad, Calif.).

The term "in combination with" as used herein means that the described agents can be administered to an animal together in a mixture, concurrently as single agents or sequentially as single agents in any order.

The term "mimetibody" as used herein means a protein having the generic formula (I):

$$(V1\text{-Pep-Lk-}V2\text{-Hg-}C_H2\text{-}C_H3)(t) \qquad (I)$$

where V1 is a portion of an N-terminus of an immunoglobulin variable region, Pep is a polypeptide that binds to cell surface TLR3, Lk is a polypeptide or chemical linkage, V2 is a portion of a C-terminus of an immunoglobulin variable region, Hg is a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10. A mimetibody can mimic properties and functions of different types of immunoglobulin molecules such as IgG1, IgG2, IgG3, IgG4, IgA, IgM, IgD and IgE dependent on the heavy chain constant domain amino acid sequence present in the construct. In some mimetibody embodiments, V1 may be absent. A mimetibody of the present invention modulates TLR biological activity through binding to TLR-expressing cells.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., *Nature* 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., *Proc. Natl. Acad. Sci. (USA)*, 86:10029-10032 (1989) and Hodgson et al., *Bio/Technology,* 9:421 (1991).

Exemplary human framework sequences useful for humanization are disclosed at, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; imgt.cines.fr; and Kabat et al., Sequences of Proteins of Immunological Interest, U.S. Dept. Health (1987), each entirely incorporated herein by reference.

Fully human mAbs lacking any non-human sequences can be prepared from human immunoglobulin transgenic mice by techniques referenced in, e.g., Lonberg et al., *Nature* 368: 856-859 (1994); Fishwild et al., *Nature Biotechnology* 14:845-851 (1996) and Mendez et al., *Nature Genetics* 15:146-156 (1997). Human mAbs can also be prepared and optimized from phage display libraries by techniques referenced in, e.g., Knappik et al., *J. Mol. Biol.* 296:57-86 (2000) and Krebs et al., *J. Immunol. Meth.* 254:67-84 (2001).

The present invention relates to TLR3 receptor binding agents capable of modulating TLR3 receptor-mediated signaling. Such binding agents include anti-TLR3 antibodies having the properties of binding a TLR3 receptor and modulating TLR3 receptor-mediated signaling.

One aspect of the invention is an antibody reactive with human Toll Like Receptor 3 (hTLR3) or hTLR3 homologs that induces cellular production of a cytokine selected from the group consisting of IL-8, MCP-1, MIP1-α, RANTES and TNF-α. These antibodies are useful as research reagents, diagnostic reagents and therapeutic agents. In particular, the antibodies of the invention are useful as therapeutic agents that can stimulate an immune response against foreign antigens.

Another aspect of the invention is an antibody reactive with hTLR3 or hTLR3 homologs that modulates a cytokine response induced by other TLR ligands. Modulation of a cytokine response results in potentiation or modification of the immune response to other TLR ligands including Cpg ODN and R848. For example, antibodies of the invention can enhance the production of Type 1 interferons such as interferon-α (IFN-α) when used in combination with TLR9 ligands such as CpG oligodinucleotides (CpG ODN).

Another aspect of the invention is an antibody reactive with hTLR3 or hTLR3 homologs that decreases the production of IL-10 produced by TLR7 agonists. For example, the antibodies of the invention significantly decrease the production of the anti-inflammatory cytokine IL-10 produced by the TLR7 agonist R848, also known as resiquimod. While not wishing to be bound to any particular theory, it is believed that the antibodies of the invention potentiate the inflammatory response to TLR7 agonists.

In one embodiment, the antibody of the invention is an isolated antibody reactive with hTLR3 having the antigen binding ability of a monoclonal antibody having the amino acid sequences of the heavy chain complementarity determining regions (CDRs) as set forth in SEQ ID NOs: 9 (CDR H1), 11 (CDR H2) and 13 (CDR H3) and the amino acid sequences of the light chain CDRs as shown in SEQ ID NOs: 19 (CDR L1), 21 (CDR L2) and 23 (CDR L3). An exemplary antibody is a monoclonal antibody having heavy chain CDR amino acid sequences as shown in SEQ ID NOs: 9, 11 and 13 and light chain CDR amino acid sequences as shown in SEQ ID NOs: 19, 21 and 23.

Another embodiment of the invention is an isolated polynucleotide encoding an antibody heavy chain having the CDR amino acid sequences shown in SEQ ID NOs: 9, 11 and 13 or a complementary nucleic acid. Other polynucleotides which, given the degeneracy of the genetic code or codon preferences in a given expression system, encode the heavy chain variable region CDRs shown in SEQ ID NOS: 9, 11 and 13 are also within the scope of the invention.

Another embodiment of the invention is an isolated polynucleotide encoding an antibody light chain having the CDR amino acid sequences shown in SEQ ID NOs: 19, 21 and 23 or a complementary nucleic acid. Other polynucleotides which, given the degeneracy of the genetic code or codon preferences in a given expression system, encode the light chain variable region CDRs shown in SEQ ID NOS: 19, 21 and 23 are also within the scope of the invention.

Another embodiment of the invention is an isolated antibody reactive with hTLR3 comprising a heavy chain having the amino acid sequence shown in SEQ ID NO: 6 and a light chain having the amino acid sequence shown in SEQ ID NO: 16.

Another embodiment of the invention is an isolated polynucleotide encoding the amino acid sequence shown in SEQ ID NO: 6 or its complement. An exemplary polynucleotide encoding the amino acid sequence shown in SEQ NO: 6 has the sequence shown in SEQ ID NO: 5.

Another embodiment of the invention is an isolated polynucleotide encoding the amino acid sequence shown in SEQ ID NO: 16 or its complement. An exemplary polynucleotide encoding the amino acid sequence shown in SEQ NO: 16 has the sequence shown in SEQ ID NO: 15.

Exemplary antibodies may be antibodies of the IgG, IgD, IgGA or IgM isotypes. Additionally, such antibodies can be post-translationally modified by processes such as glycosylation, isomerization, aglycosylation or non-naturally occurring covalent modification such as the addition of polyethylene glycol moieties (pegylation) and lipidation. Such modifications may occur in vivo or in vitro. Fully human, humanized and affinity-matured antibody molecules or antibody fragments are within the scope of the invention as are mimetibodies, fusion proteins and chimeric proteins.

The antibody of the invention may bind hTLR3 with a $K_d$ less than or equal to about $10^{-7}$, $10^{-8}$, $10^{-9}$, $10^{-10}$, $10^{-11}$ or $10^{-12}$ M. The affinity of a given molecule for a hTLR3 receptor can be determined experimentally using any suitable method. Such methods may utilize Biacore or KinExA instrumentation, ELISA or competitive binding assays known to those skilled in the art.

Antibody molecules binding a given TLR3 homolog with a desired affinity can be selected from libraries of variants or fragments by techniques including antibody affinity maturation and other art-recognized techniques suitable for non-antibody molecules.

Another embodiment of the invention is a vector comprising at least one polynucleotide of the invention. Such vectors may be plasmid vectors, viral vectors, transposon based vectors or any other vector suitable for introduction of the polynucleotides of the invention into a given organism or genetic background by any means.

Another embodiment of the invention is a host cell comprising any of the polynucleotides of the invention such as a polynucleotide encoding a polypeptide comprising SEQ ID NO: 9, SEQ ID NO: 11 and SEQ ID NO: 13 and a polynucleotide encoding a polypeptide comprising SEQ ID NO: 19, SEQ ID NO: 21 and SEQ ID NO: 23. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1 (ATCC CRL-61) or DG44.

Another embodiment of the invention is a method of making an antibody of the invention comprising culturing a host cell of the invention and recovering the antibody produced by the host cell. Such an antibody may be the hTLR3 antibody exemplified below as mAb C1130 having heavy and light amino acid sequences as shown in SEQ ID NOs: 6 and 16, respectively.

The ability of the antibodies of the invention to potentiate CpG-mediated IFN-α production provides for various combination-type therapies. For example, the use of an antibody of the invention in combination with foreign antigens such as TLR agonist molecules or vaccine antigens will modulate an immune response and be useful in treating infections. Thus, another aspect of the invention is the use of an antibody of the invention in combination with other immune stimulants such as interferon or TLR9 agonists including, but not limited to, CpG ODN to stimulate and sustain an immune response as measured by enhanced production of Type I IFN (e.g., IFNα) to prevent or treat viral infections including hepatitis viruses, herpes simplex virus, human immunodeficiency virus and human papilloma virus and other cutaneous and mucosal-associated infections. Also, the invention provides for use of an antibody of the invention in combination with other immune stimulants such as interferon or TLR9 agonists including, but not limited to, CpG ODN to treat cancers including multiple myeloma, chronic myelogenous leukemia, hairy cell leukemia, malignant melanoma, and sarcomas (including Kaposi's sarcoma). Further, the invention also provides for the use of an antibody of the invention in combination with other immune stimulants such as interferon or TLR9 agonists including but not limited to CpG ODN to treat inflammatory bowel diseases (e.g., Crohn's disease and ulcerative colitis).

Another aspect of the invention is the use of an antibody of the invention in combination with a TLR7 agonist such as R848 (resiquimod) or imiquimod to provide for a combination therapy to prevent or treat viral infection-associated symptoms such as genital warts. The synthetic TLR7 agonist imiquimod has been approved by regulatory authorities for the treatment of genital warts. Another aspect of the invention is the use of an antibody of the invention in combination with TLR9 or TLR7 agonists to prevent or treat pulmonary diseases including bacterial, fungal and viral pneumonias, and pathogen-mediated exacerbation of pulmonary diseases such as asthma, bronchitis and chronic obstructive pulmonary diseases. Yet another aspect of the invention is the use of an antibody of the invention in combination with TLR9 or TLR7 agonists to prevent or treat graft-versus-host disease (GVHD). Yet another aspect of the invention is the use of an antibody of the invention in combination with immune treatments, such as interferon, to prevent or treat autoimmune diseases, including multiple sclerosis and lupus.

The methods of the invention may be used to treat an animal belonging to any genus. Examples of such animals include humans, mice, birds, reptiles, and fish.

Amounts of a given TLR3 antibody sufficient to treat a given condition can be readily determined. In the method of the invention the TLR3 antibody may be administered singly or in combination with at least one other TLR agonist molecule or vaccine antigen.

The mode of administration for therapeutic use of the antibodies of the invention may be any suitable route that delivers the agent to the host. The proteins, antibodies, antibody fragments and mimetibodies and pharmaceutical compositions of these agents are particularly useful for parenteral administration, i.e., subcutaneously, intramuscularly, intradermally, intravenously or intranasally.

Antibodies of the invention may be prepared as pharmaceutical compositions containing an effective amount of the antibody as an active ingredient in a pharmaceutically acceptable carrier. An aqueous suspension or solution containing the antibody, preferably buffered at physiological pH, in a form ready for injection is preferred. The compositions for parenteral administration will commonly comprise a solution of the antibody of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antibody of the invention. Actual methods for preparing parenterally administrable compositions are well known and are described in more detail in, for example, "Remington's Pharmaceutical Science", 15th ed., Mack Publishing Company, Easton, Pa.

The antibodies of the invention, when in a pharmaceutical preparation, can be present in unit dose forms. The appropriate therapeutically effective dose can be determined readily by those of skill in the art. A determined dose may, if necessary, be repeated at appropriate time intervals selected as appropriate by a physician during the treatment period.

The antibodies of the invention can be lyophilized for storage and reconstituted in a suitable carrier prior to use. This technique has been shown to be effective with conventional immunoglobulins and protein preparations and art-known lyophilization and reconstitution techniques can be employed.

The present invention will now be described with reference to the following specific, non-limiting examples.

EXAMPLE 1

Generation of Anti-TLR3 mAbs

The anti-TLR3 mAb was generated using standard hybridoma technology in normal Balb/c mice (Kohler et al., *J Immunol* 6:511-519, 1976). All animal procedures were performed in accordance with the guidelines established by the Institutional Animal Care and Use Committee. The mice were injected intradermally twice with plasmid DNA encoding amino acids 1-703 of human TLR3 (SEQ ID NO: 3). Amino acids 1-703 correspond to the predicted extracellular domain of hTLR3 (SEQ ID NO: 4). The mice received the plasmid DNA injections of 10 μg/mouse two weeks apart. The mice were boosted by intradermal injection with the extracellular domain of the purified recombinant human TLR3 protein. The first and second protein immunizations, with 15 μg protein, occurred two and four weeks after the second plasmid DNA injection. The third boost (10 μg protein) occurred five months later. Three days prior to the harvest of the spleens, the mice were injected intravenously with the TLR3 protein (15 μg/mouse). B cell fusions were performed using standard methods (Kohler et al., supra). Hybridomas were selected using media containing hypoxanthine-aminopterin-thymidine. Wells were screened by ELISA to detect anti-TLR3 antibodies. Positive wells were expanded and cloned using limiting dilution. A large batch of antibody was prepared and purified using a Protein G column. The endotoxin levels were confirmed to be <1 EU/mg. mAb C1130 was generated in this manner. The antibody sequence is shown in FIGS. 1 and 2.

EXAMPLE 2

Isolation of Human Peripheral Blood Mononuclear Cells

PBMCs were isolated from human blood. Whole blood was collected from a human donor into heparin-coated syringes. Approximately 50 mL of sterile Hank's Balanced Salt Solution (HBSS) (Invitrogen) was added to every 100 mL of blood. Thirty-eight mL of blood:HBSS were added to a 50 mL conical tube and 11 mL Ficoll-Paque Plus solution (Amersham) was slowly layered underneath. The tubes were centrifuged at 400×g for 40 minutes at room temperature. The centrifuge brake was turned off to preserve the gradient. The PBMCs form a white layer just above the Ficoll. The PBMCs from one conical were aspirated with a pipette into a new 50 mL conical. The tube was filled with HBSS to wash away the remainder of the Ficoll. The cells were spun at 600×g for 10 minutes. The supernatant was poured off and the pellet was resuspended in 10 mL Red Blood Cell Lysis Solution (Sigma) in a single tube. The tube was incubated at room temperature for ten minutes. The tube was brought to 50 mL with HBSS, and the cells were pelleted by centrifugation at 600×g. The cells were washed twice more with HBSS. After the final wash the pellet was resuspended in complete media: RPMI 1640 media/10% FBS/1× Non-Essential Amino Acids/1× Sodium Pyruvate/10 ug/mL gentamycin. Gentamycin was purchased from Sigma; the other media components were purchased from Invitrogen. An aliquot of the cells was removed and mixed with 50 μL trypan blue to obtain a live cell count. The cells were plated in 48-well plates at a concentration of $3\times10^6$ cells/well (0.5 mL/well).

EXAMPLE 3

Determination of Anti-hTLR3 Antibody Effects on Cytokine/Chemokine Production

Purified antibodies were added to PBMCs to a final concentration of 20 μg/mL. The cells and the antibodies were incubated at 37° C. for 30 minutes to one hour before the addition of 1 μg/mL CpG2216 (synthesized by Invitrogen), or 1 μg/mL R848 (Invivogen). CpG2216 has the sequence 5'-ggG GGA CGA TCG TCg ggg gg-3'. The bases in capital letters are linked by phosphodiester bonds and those in lowercase are linked by phosphorothioate bonds. R848, also known as resiquimod, is an imidazoquinolinamine, and is in the same compound class as imiquimod. Supernatants were harvested after 24 h and frozen at −20° C.

Cytokine and chemokine concentrations in the supernatants were measured using Luminex technology. A Luminex Kit from Biosource was used to measure the following cytokines/chemokines: IL-1β, IL-6, IL-8, IL-10, IL-12, TNFα, IFNα, IFNγ, RANTES, MCP-1, MIP-1α and IP-10. In some instances, IFNα levels were measured using an ELISA kit (PBL Biomedical Labs). Statistical analysis was performed using two-factor analysis of variance with follow-up pairwise comparisons.

The results are shown in FIG. 3 and indicate that incubation of PBMCs with C1130 resulted in the production of IL-8, MCP-1, MIP-1 α, RANTES, and TNF α by the human cells (n=3 experiments). These effects were not seen in PBMCs incubated with another anti-TLR3 murine IgG1 antibody, C1068 that was generated in a similar manner to C1130. Lots of purified antibody were tested for endotoxin and the levels were below 1 EU/mg.

EXAMPLE 4

Determination of Anti-hTLR3 Antibody Effects on IFNα Production

Figure 4:
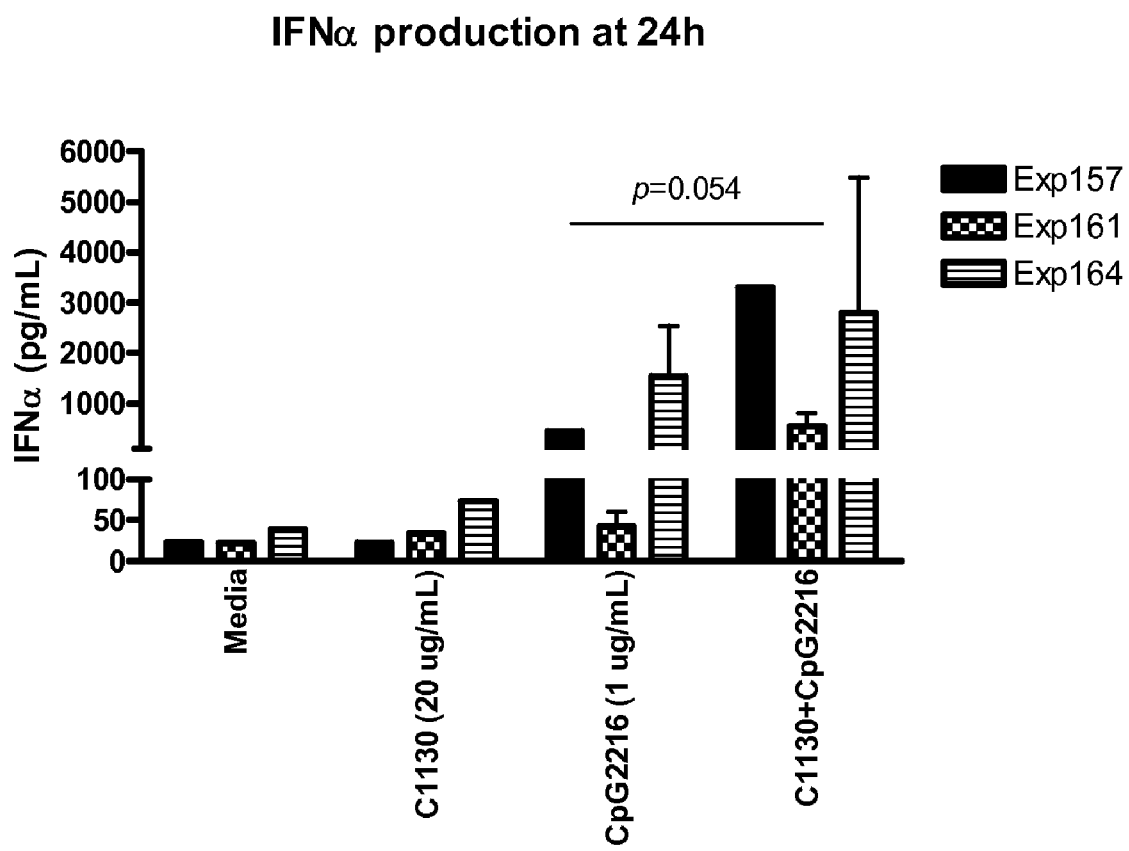
FIG. 4 shows C1130 enhanced CpG-induced IFNα production at 24 h.

Since some TLRs are known to dimerize and/or use different adaptor proteins to alter ligand-binding specificity, PBMCs that were pretreated with the anti-hTLR3 antibody C1130 were stimulated with ligands for other TLRs, in particular CpG2216 as described in Example 3 to examine the effect of TLR3 modulation on the response to other TLR ligands. Since the ligands for TLR3 and TLR9 are nucleic acids, and both activate interferon secretion, it was hypothesized that they could share a signaling pathway. The results from three experiments are shown in FIG. 4 and indicate that PBMCs incubated with C1130 and CpG2216 secreted more IFNα than cells stimulated with CpG alone. The average increase was 7-fold.

EXAMPLE 5

Determination of Anti-hTLR3 Antibody Effects on IL10 Production

Figure 5:
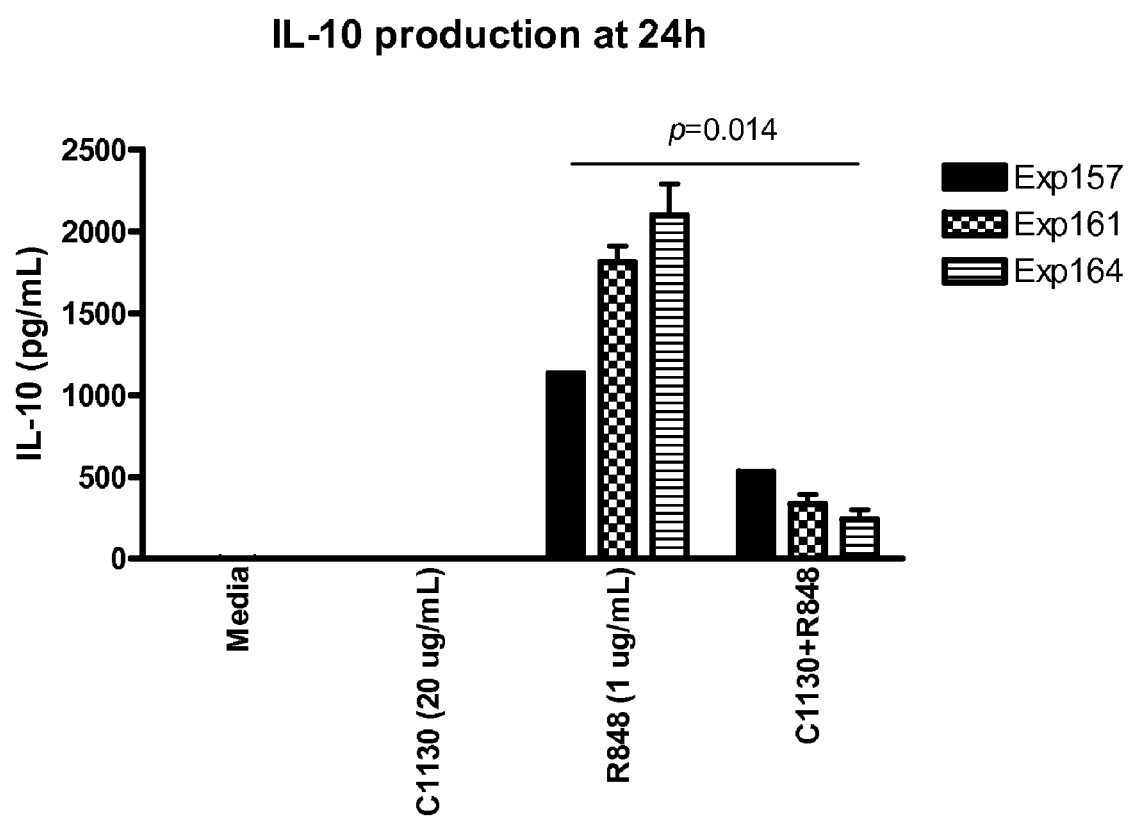
FIG. 5 shows C1130 decreased R848-induced IL-10 production at 24 h.

The ligands for TLR7 and TLR8 are also nucleic acids. R848 (resiquimod) is a synthetic ligand for TLR7 and TLR8 in humans, which have been shown to recognize guanosine- and uridine-rich single-stranded RNA (Heil et al., Science 5663: 1526, 2004) and was used to stimulate human PBMCs. Activation of TLR7, like TLR3, triggers the secretion of Type-I interferons. The results in FIG. 5 indicate that C1130 did not affect levels of IFNα secreted by PBMCs in response to R848. Though PBMCs usually secrete very high levels of IFNα in response to R848, in two of three experiments stimulation with R848 induced the production of ~500 pg/mL IFNα (a level low enough to presumably see any effect by an agonist or antagonist mAb). C1130 did affect R848-induced IL-10 levels. In three experiments, C1130 decreased R848-induced IL-10 by an average of 5-fold.

EXAMPLE 6

Recognition of Epithelial Cell Surface TLR3 by Antibody C1130

Flow cytometry analyses were conducted on a Fluorescence-Activated Cell Sorter (FACS) instrument. C1130 antibody was conjugated to APC using a Zenon mouse IgG1 labeling kit according to the manufacturer's protocol. Five microliters of labeling reagent per 1 μg of mAb were incubated for 5 minutes at room temperature and protected from light. Blocking reagent was added at a ratio of 5 μl to 1 μg of mAb according to the manufacturer's protocol. Zenon-labeled antibodies were used within 30 minutes of conjugation. HEK293 (human embryonic kidney epithelial cells) that were stably transfected with human TLR3 were purchased from Invivogen.

293-TLR3 were fixed by 15 minute incubation in Cytofix either prior to or following staining. Approximately $1 \times 10^6$ cells in 50 μl were incubated with APC-labeled antibody in 96-well round bottom plate for 30-60 minutes on ice. Cells were washed 3 times in PBS+1% FBS by centrifugation at 1600 rpm for 2 minutes. Data acquisition was performed on a Becton-Dickinson FACSCalibur instrument and data analysis was performed using WinList (Verity Software House, Topsham, Me.).

Figure 6:
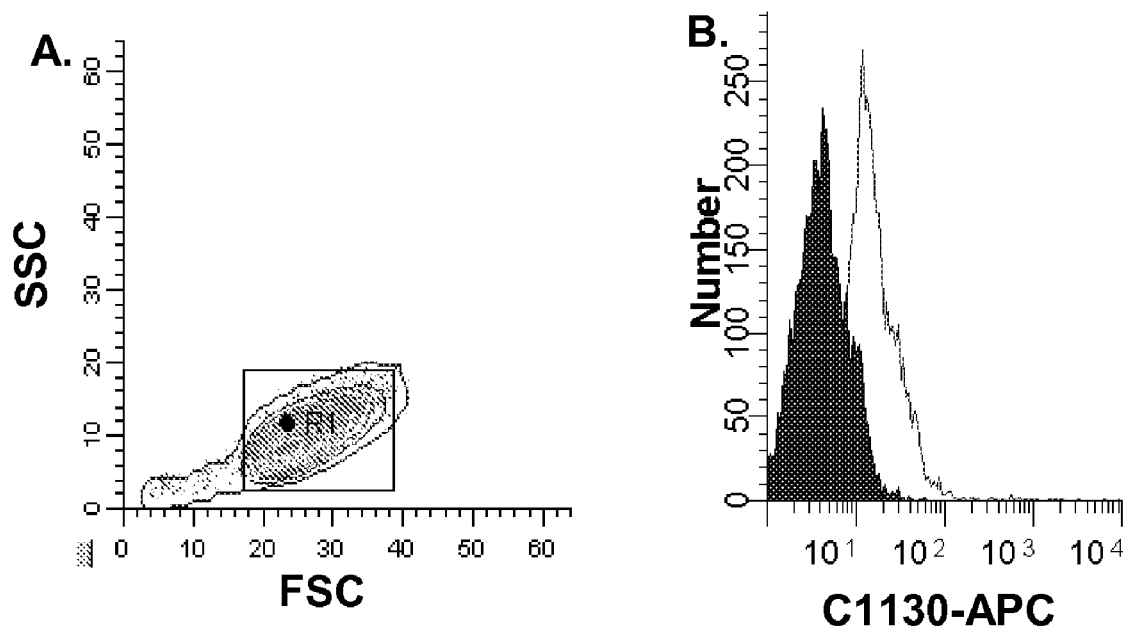
FIG. 6 shows C1130 recognition of cell-surface TLR3 on stably transfected HEK293 cells.

The results in FIG. 6 show that antibody C1130 binds to surface TLR3 on 293-hTLR3 cells fixed either before or after staining. A commercially available PE-labeled anti-hTLR3 (clone 3.7) was used as a positive control and Zenon APC-labeled mouse IgG1 as a negative control. These data demonstrate that the anti-hTLR3 antibody C1130 recognizes epithelial cells.

EXAMPLE 7

Recognition of Lung Epithelial Cell Surface TLR3 by Antibody C1130

A549 cells, a human lung epithelial cell line, were obtained from the American Type Culture Collection (ATCC Accession No. CCL-185). Cells were transfected with a mammalian expression vector encoding a neomycin selectable marker along with a full-length copy of the human TLR3 gene under the control of the cytomegalovirus (CMV) promoter using Lipofectamine 2000 reagent (Invitrogen, Inc). A549 cells were also transfected in parallel with the vector plasmid DNA-only (encoding neomycin resistance) as a control. Twenty-four hours post-transfection, cells were then trypsinized and seeded at dilution of 1:20 in media containing neomycin (G418) at 0.5 mg/ml. Cell clones appeared after 2 weeks growth in selection media containing G418. Cell colonies from each transfection were separately pooled. A549 cell lines derived from transfection and selection with the full-length human TLR3 expression vector (A549-hTLR3) or vector control (A549-neo) were maintained in growth media containing 0.5 mg/ml of G418.

Figure 7:
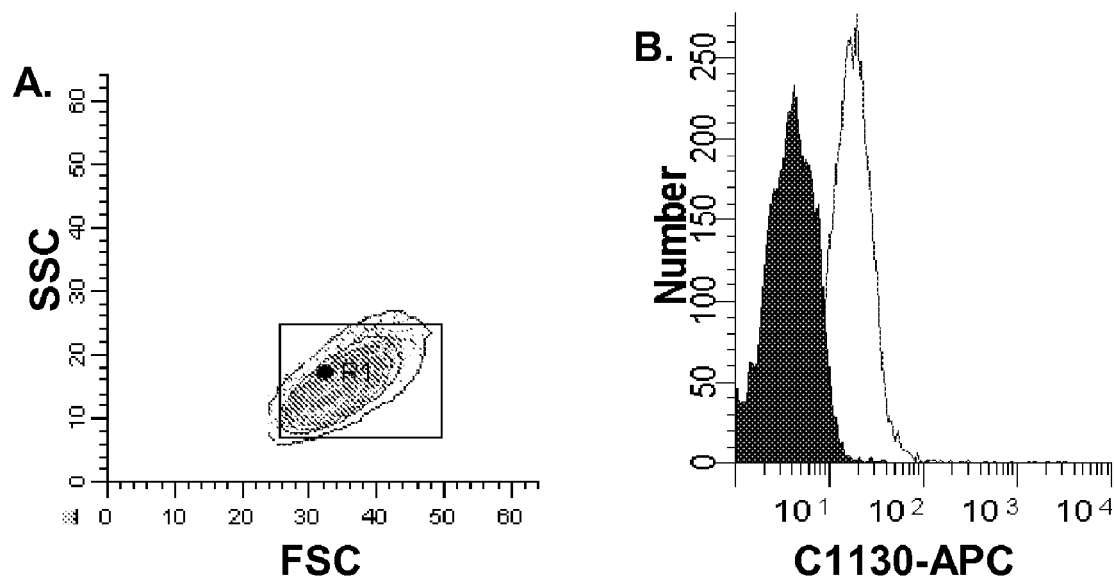
FIG. 7 shows C1130 recognition of cell-surface TLR3 on stably transfected A549-TLR3.2 cells.

C1130 antibody was conjugated to APC as described in Example 7. A549-TLR3.2 cells were fixed by 15 minute incubation in Cytofix either prior to or following staining. Approximately $1 \times 10^6$ cells in 50 μl were incubated with APC-labeled antibody in 96-well round bottom plate for 30-60 minutes on ice. Cells were washed 3 times in PBS+1% FBS by centrifugation at 1600 rpm for 2 minutes. Data acquisition and analysis was performed as described in Example 7. The results in FIG. 7 shows that C1130 binds to surface TLR3 on A549-TLR3.2 cells fixed either before or after staining. A commercially available PE-labeled anti-TLR3 (Clone 3.7) was used as a positive control and Zenon APC-labeled mouse IgG1 as a negative control. The ability of C1130 to recognize lung epithelial cells indicates that it has potential therapeutic use in pulmonary infections.

EXAMPLE 8

Recognition of Cynomolgus White Blood Cells by Antibody C1130

Whole blood from Cynomolgus macaques was diluted 1:10 in FACSLyse buffer and incubated for 15 minutes at room temperature to lyse the red blood cells. Cells were then washed in PBS+1% FBS 4 times by centrifugation at 1400 rpm for 8 minutes. The resulting cell pellet was resuspended in PBS+1% FBS and counted manually using a hemacytometer. Cell viability was determined by staining a sample cell population with 0.2% trypan blue. All samples tested were at least 95% viable.

The total cell pellet was resuspended in 1-2 ml of PBS supplemented with 10% FBS and kept at either 4° C. or 37° C.

to evaluate for differences in receptor internalization. Fifty microliters (approximately 2×10$^6$ cells) were distributed to each well in 96-well round bottom plates. FITC, PE and APC labeled mAbs were added at 1 μg per well, incubated for at least 30 minutes at either 4° C. or 37° C. and protected from light. Cells were then washed 3 times in PBS+1% FBS by centrifugation at 1600 rpm for 2 minutes. After the final wash the cells were resuspended in Cytofix buffer and incubated for 15 minutes at either 4° C. or 37° C. Following paraformaldehyde fixation in the Cytofix buffer, the cells were washed once by centrifugation at 1600 rpm for 2 minutes and resuspended in 200 μl of PBS+1% FBS. Samples were either read immediately or stored overnight at 4° C. before acquisition. Data acquisition and analysis was performed as described in Example 7.

Figure 8:
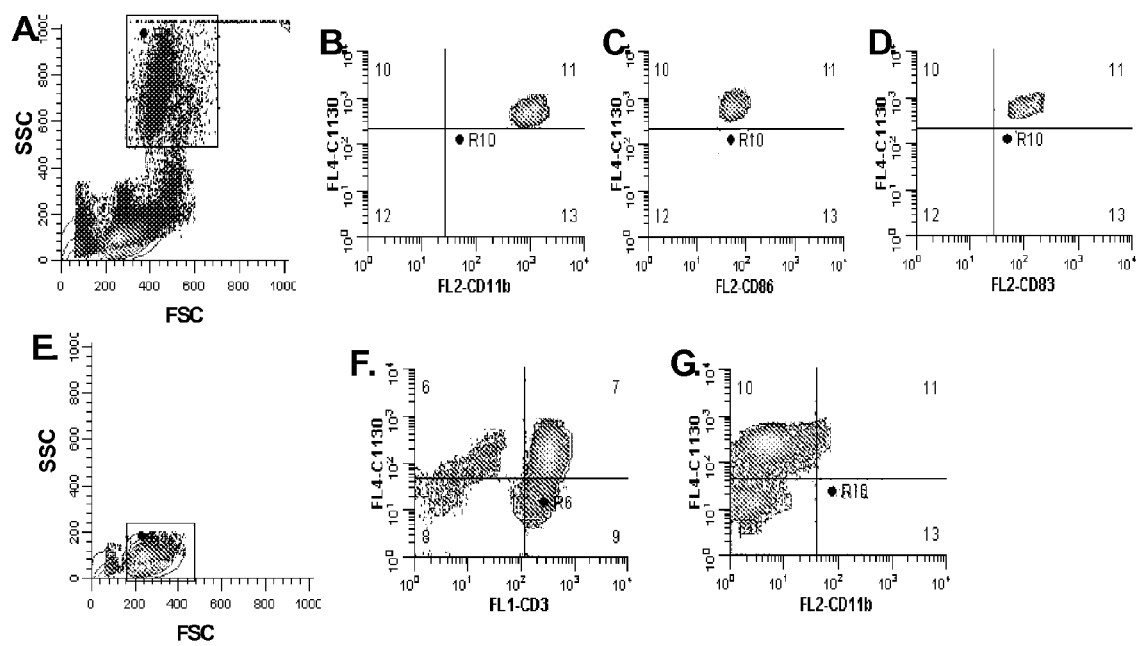
FIG. 8 shows C1130 recognition of Cynomolgus macaque PBMCs.

The results shown in FIG. 8 indicate that C1130 binds to cynomolgus macaque (cyno) CD11b positive cells, CD83 positive cells, CD86 positive cells, and CD3 positive cells. CD83 is found on B cells and dendritic cells and CD3 is found only on T-cells, indicating that C1130 recognizes different cell populations in PBMCs.

The present invention now being fully described, it will be apparent to one of ordinary skill in the art that many changes and modifications can be made thereto without departing from the spirit or scope of the appended claims.

The invention claimed is:

1. An isolated antibody reactive with hTLR3 comprising the amino acid sequences of the heavy chain complementarity determining regions (CDRs) as shown in SEQ ID NOs: 9 (CDR H1), 11 (CDR H2) and 13 (CDR H3) and the amino acid sequences of the light chain CDRs as shown in SEQ ID NOs: 19 (CDR L1), 21 (CDR L2) and 23 (CDR L3).

2. An isolated antibody reactive with hTLR3 comprising a heavy chain comprising the amino acid sequence shown in SEQ ID NO: 6 and a light chain comprising the amino acid sequence shown in SEQ ID NO: 16.

3. A hybridoma cell line that produces the antibody of claim 2.

* * * * *